United States Patent
Bugge

[11] Patent Number: 5,824,068
[45] Date of Patent: Oct. 20, 1998

[54] CARDIAC VALVE HOLDERS

[75] Inventor: Mogens Bugge, Göteborg, Sweden

[73] Assignee: St. Jude Medical, Inc., St. Paul, Minn.

[21] Appl. No.: 908,193

[22] Filed: Aug. 7, 1997

Related U.S. Application Data

[63] Continuation of Ser. No. 663,303, filed as PCT/SE94/01247, Dec. 22, 1994, abandoned.

[30] Foreign Application Priority Data

Dec. 22, 1993 [SE] Sweden .................................. 9304234
Sep. 13, 1994 [SE] Sweden .................................. 9403043

[51] Int. Cl.⁶ ........................................................ A61F 2/24
[52] U.S. Cl. ................................. 623/2; 606/99; 606/108
[58] Field of Search .................................... 623/2, 3, 900; 606/1, 99, 108

[56] References Cited

U.S. PATENT DOCUMENTS

| | | | |
|---|---|---|---|
| Re. 30,507 | 2/1981 | Kaster ............................................. | 3/1.5 |
| 3,409,013 | 11/1968 | Berry ............................................. | 128/303 |
| 3,546,710 | 12/1970 | Shumakov et al. ........................... | 3/1 |
| 3,574,865 | 4/1971 | Hamaker ........................................ | 3/1 |
| 3,763,548 | 10/1973 | Anderson ...................................... | 29/445 |
| 3,828,787 | 8/1974 | Anderson et al. ............................. | 128/303 |
| 3,839,741 | 10/1974 | Haller ............................................. | 3/1 |
| 3,860,005 | 1/1975 | Anderson et al. ............................. | 128/303 |
| 3,997,923 | 12/1976 | Possis ............................................. | 3/1.5 |
| 4,078,268 | 3/1978 | Possis ............................................. | 3/1.5 |
| 4,101,031 | 7/1978 | Cromie .......................................... | 206/438 |
| 4,182,446 | 1/1980 | Penny ............................................ | 623/2 |
| 4,197,593 | 4/1980 | Kaster et al. ................................... | 3/1.5 |
| 4,211,325 | 7/1980 | Wright ........................................... | 623/2 |
| 4,599,081 | 7/1986 | Cohen ........................................... | 623/2 |
| 4,655,218 | 4/1987 | Kulik et al. ................................... | 128/321 |
| 4,680,031 | 7/1987 | Alonso .......................................... | 623/2 |
| 4,683,883 | 8/1987 | Martin ........................................... | 128/303 |
| 4,705,516 | 11/1987 | Barone et al. ................................. | 623/2 |
| 4,755,181 | 7/1988 | Igoe ............................................... | 623/2 |
| 4,790,843 | 12/1988 | Carpentier et al. ........................... | 623/2 |
| 4,801,015 | 1/1989 | Lubock et al. ................................ | 206/438 |
| 4,863,460 | 9/1989 | Magladry ...................................... | 623/2 |
| 4,865,600 | 9/1989 | Carpentier et al. ........................... | 623/2 |
| 4,932,965 | 6/1990 | Phillips ......................................... | 623/2 |
| 5,071,431 | 12/1991 | Sauter et al. .................................. | 623/2 |
| 5,104,406 | 4/1992 | Curcio et al. ................................. | 623/2 |
| 5,163,954 | 11/1992 | Curcio et al. ................................. | 623/2 |
| 5,197,980 | 3/1993 | Gorshkov et al. ............................ | 623/2 |
| 5,201,880 | 4/1993 | Wright et al. ................................. | 623/2 |
| 5,236,450 | 8/1993 | Scott ............................................. | 623/2 |
| 5,354,330 | 10/1994 | Hanson et al. ................................ | 623/2 |
| 5,370,685 | 12/1994 | Stevens ......................................... | 623/2 |
| 5,403,305 | 4/1995 | Sauter et al. .................................. | 606/1 |
| 5,425,705 | 6/1995 | Evard et al. .................................. | 604/28 |
| 5,433,700 | 7/1995 | Peters ............................................ | 604/4 |
| 5,443,502 | 8/1995 | Caudillo et al. .............................. | 623/2 |
| 5,480,425 | 1/1996 | Ogilive ......................................... | 623/2 |
| 5,531,785 | 7/1996 | Love et al. .................................... | 623/2 |
| 5,582,607 | 12/1996 | Lackman ...................................... | 606/1 |
| 5,713,952 | 2/1998 | Vanney et al. ................................ | 623/2 |

FOREIGN PATENT DOCUMENTS

| | | |
|---|---|---|
| 1 690 738 A1 | 4/1989 | U.S.S.R. . |
| 1 690 739 A1 | 11/1991 | U.S.S.R. . |
| 2 181 057 | 4/1987 | United Kingdom . |
| 91/17720 | 11/1991 | WIPO . |
| 92/12688 | 8/1992 | WIPO . |
| 94/18881 | 9/1994 | WIPO . |
| 95/15715 | 6/1995 | WIPO . |
| 95/17139 | 6/1995 | WIPO . |

OTHER PUBLICATIONS

"Aortic Valve Instructions For Handling and Use", by Medical Incorporated, Mar. 1976.

*Primary Examiner*—Michael J. Milano
*Assistant Examiner*—Tram A. Nguyen
*Attorney, Agent, or Firm*—Hallie A. Finucane, Esq.; Westman, Champlin & Kelly, P.A.

[57] ABSTRACT

A holder for an artificial heart valve includes a holder body, a handle, and a safety member. The holder body is configured to selectively couple to the heart valve. The handle extends from the holder body. The safety member is spaced apart from the holder body, and extends from the handle and is configured to mate with the heart valve in exactly one orientation. The safety member prevents the holder body from mating with the heart valve in other orientations.

13 Claims, 4 Drawing Sheets

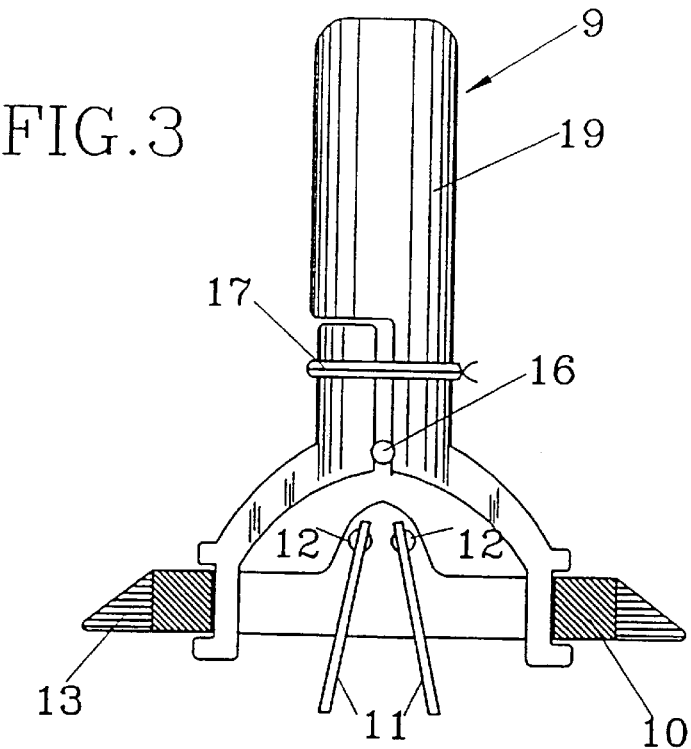
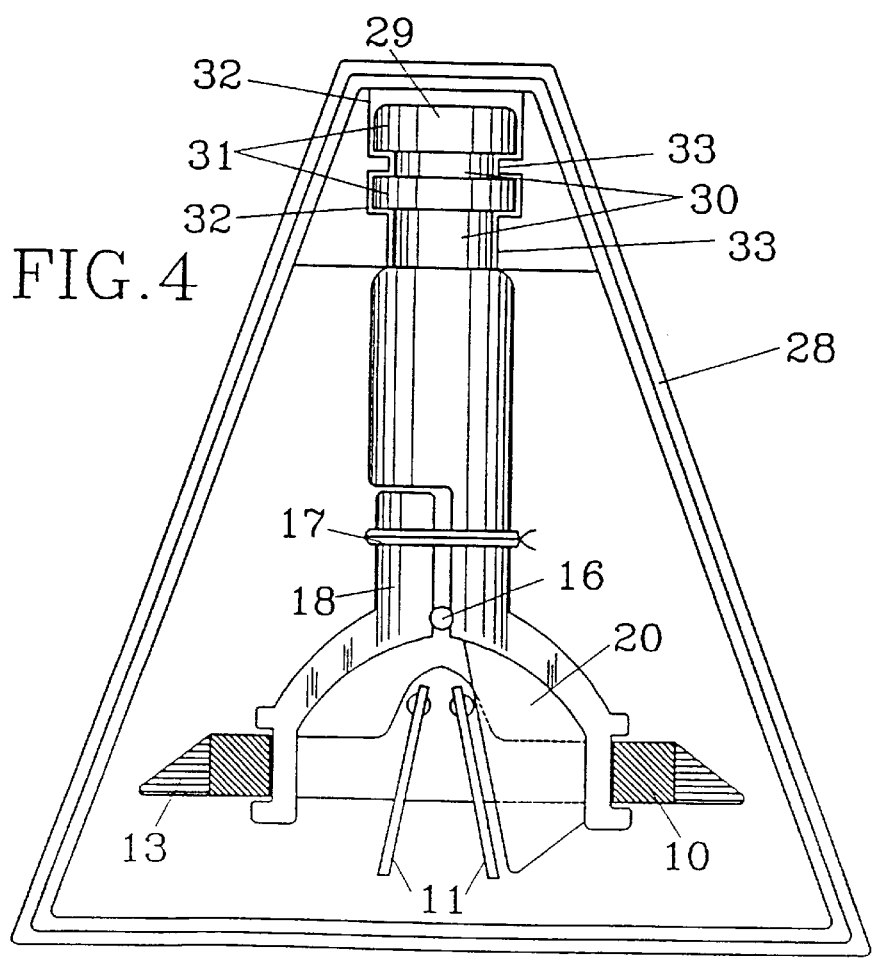

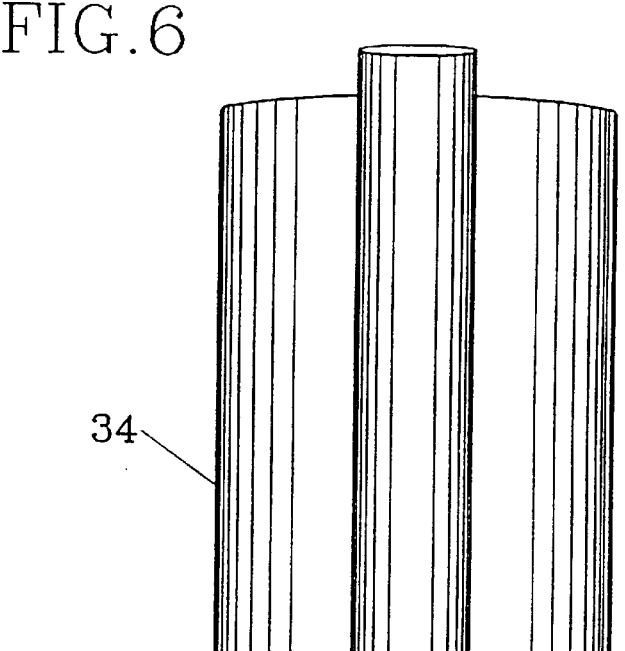
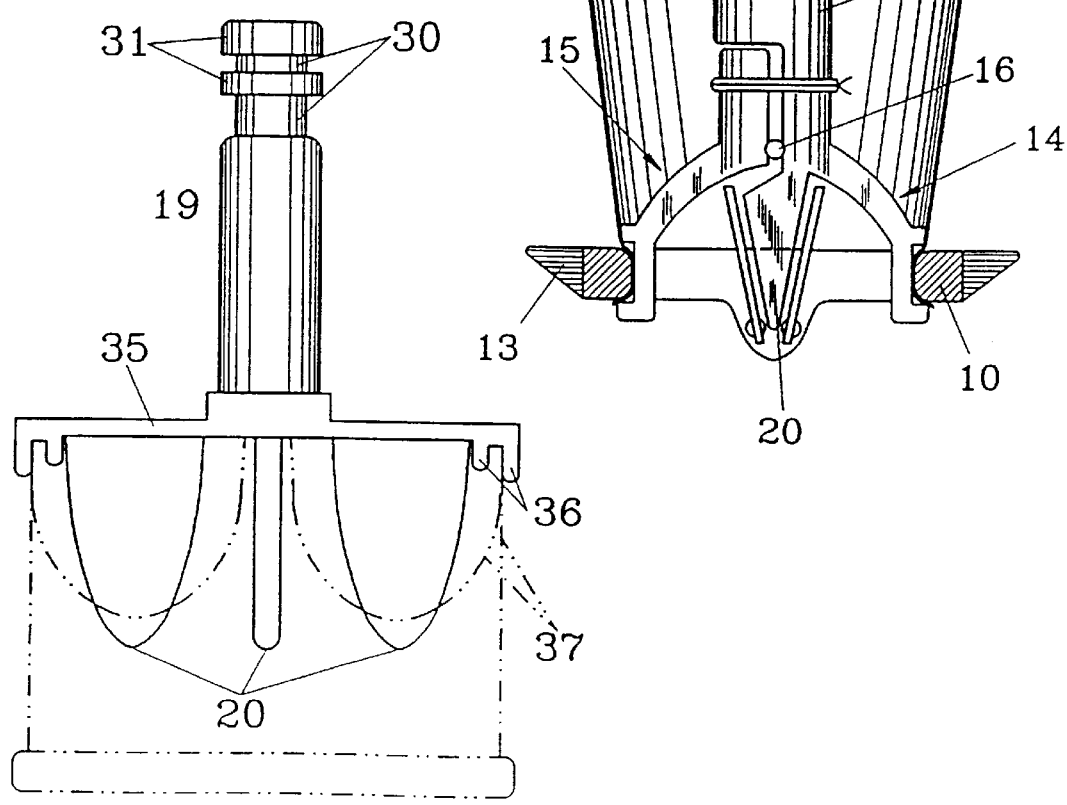

CARDIAC VALVE HOLDERS

This is a File Wrapper Continuation of application Ser. No. 08/663,303, filed as PCT/SE94/01247, Dec. 22, 1994, now abandoned.

The present invention relates to a holder for artificial heart valves, of the type which is firmly but detachably attached to the valve and which is intended to be removed after the valve is correctly placed or operated inside the patient, by breaking a transportation safety whereby the partial foldable holder can be removed

BACKGROUND OF THE INVENTION

Within cardiac surgery, about 20% of the operations are for the implantation of artificial heart valves. Considering the entire world, this implies implantation of at least 100,000 valves per year.

Heart valves are supplied in different sizes from factories in small transportation containers. For each product there is a prosthesis sizer to measure which size to fit into the actual heart. When the test is finished, the actual size and type of valves are obtained and the implantation is carried out.

A holder for artificial heart valves is used for both mechanical valves and for biological valves. The purpose of the holder is to:
1) fix the valve in its container during the transportation, and
2) serve as a handle for a cardiac surgeon and his operation team during the implantation.

There are two main types of valves: a) aortic valves and b) mitral valves. Moreover, these are produced in several different sizes.

If the wrong size or type of valve is used, results can be disastrous, and therefore the identification of the valves are surrounded by security procedures at the operation time.

It is consequently very important that the valves, which are much alike, are implanted in the heart in the correct way and in the correct position, since an incorrectly placed valve can cause death of the patient. Therefore, aortic valves and mitral valves should not be mixed, which can happen in several ways. For example, implanting a mitral valve in an aortic position, or the aortic valve in a mitral position. Another example is implanting a valve turned the wrong way (up and down), which is possible in both positions.

Another type of error that can occur is wrong packing of the product at the factory. Usually, there is an adhesive label on the transport packaging, which indicates the content. At the factory the packaging is surrounded by several security procedures to ensure that the content of the container corresponds to the label on the container.

Another problem with heart valve operations is that the holder or the prosthesis sizer breaks and may leave fragments inside the heart. Also, it has occurred that the entire holder has been forgotten in the heart, where the surgeon believes that it is a part of the heart valve.

THE OBJECTS OF THE INVENTION AND MOST IMPORTANT FEATURES

The object of the present invention is to provide a holder for the heart valve that as much as possible eliminates or reduces such mistakes or problems as mentioned above. Another object of the invention is to prevent the incorrect packaging of the valves provided with the holder already at the production stage, and a third object is to be able to detect a holder or a part thereof, which during the operation could have been dropped.

DESCRIPTION OF THE DRAWINGS

FIG. 3 shows a cross-sectional view of a conventional standard holder for a mitral valve.

FIG. 4 shows a cross-sectional view of a holder with a heart valve for the mitral position according to the present invention placed in a transportation container.

FIG. 6 shows a holder according to FIG. 2 with an aortic prosthesis rigidly sewn to the heart valve.

FIG. 7 shows a holder for a biological heart valve in the aortic position.

DESCRIPTION OF THE EMBODIMENTS

Figure 1:
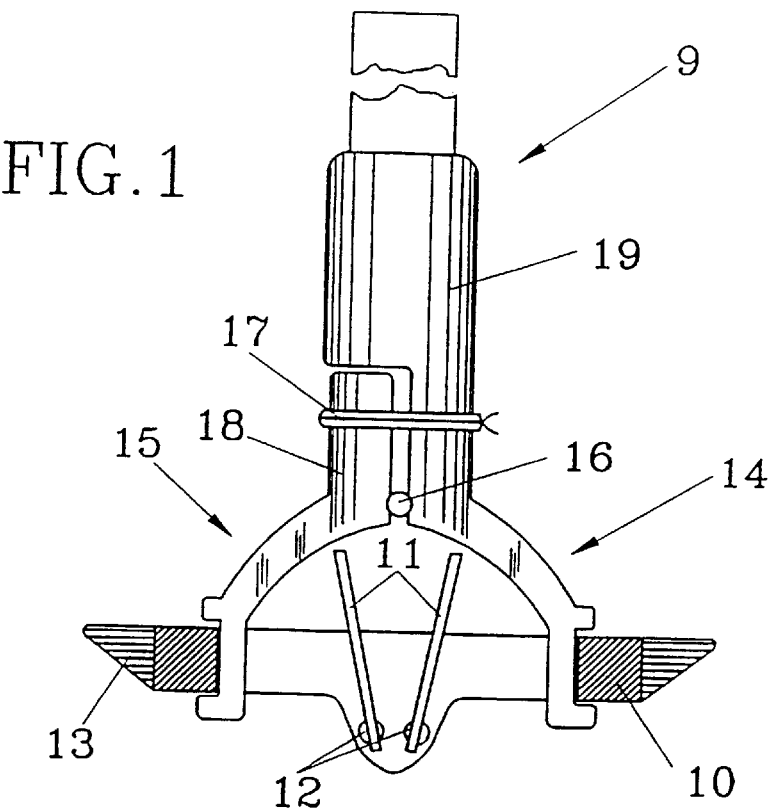
FIG. 1 schematically shows, in a cross-sectional view of a conventional standard holder and an artificial aortic valve.

The invention is exemplified below for mechanical valves of double blade or leaflet type, but the same principles can of course be applied to any type of valve holder.

The heart valve itself consists of a valve ring 10, in which two semicircular valve blades 11 are mounted, each on a joint axis 12. Exterior to the valve ring 10 there is a valve cuff 13, which is the 'soft' part of the valve, which is sewn firmly (sutured) to the heart.

A valve holder 9 in this example consists of two parts 14 and 15, which are mutually united through a joint 16. The holder 9 is mounted on the valve ring 10 with the valve blade or leaflet in an open position and after mounting, the two parts are held together by a suture 17 around the two handle portions 18,19 of the holder. To remove the holder from the valve, suture 17 is cut and the holder is opened through the joint 16.

Figure 2:
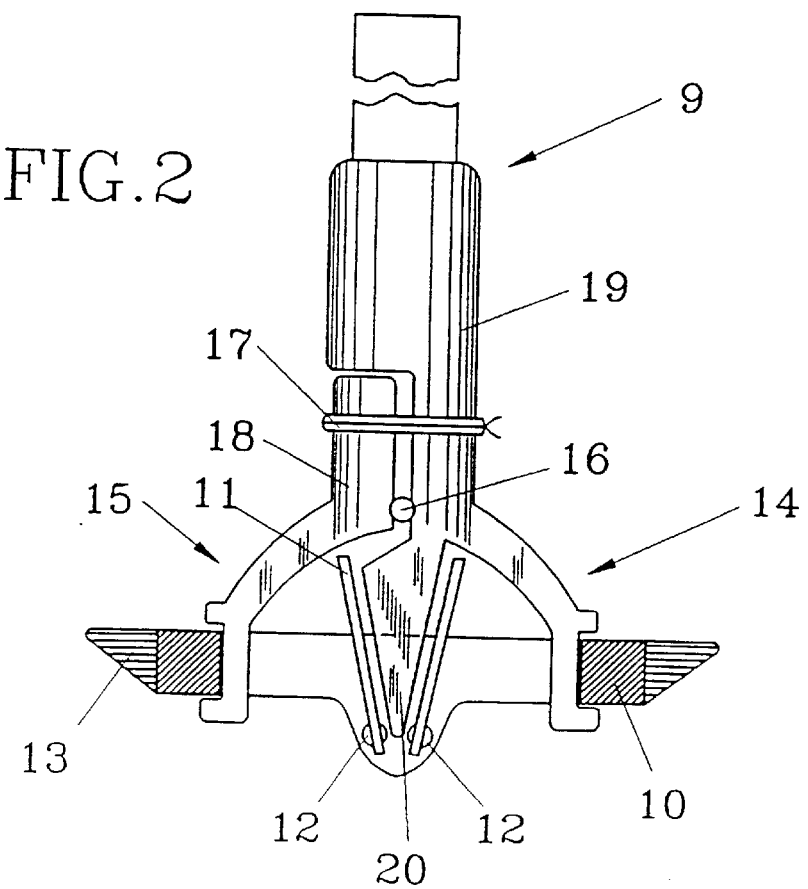
FIG. 2 shows a cross-sectional view of a holder with a heart valve in an aortic position according to the present invention.

As shown in FIG. 2 safety member 20 is provided by means of an extension from the handle portion 19, which continues downwards between two blades 11 of the heart valve in the aortic case, (FIG. 2), and along one side of a blade 11 in the mitral case (FIG. 4), respectively.

Preferably, the holder 9 for the aortic and mitral valves is provided with different colors or color codes, e.g., red for an aortic holder and blue for a mitral holder. This will provide a clear indication for a person who handles the valve. If the person in question is color-blind or does not know the color coding, the holder, valve and packaging are marked with identification symbols. The holder 9 is so designed that it fits into the valve only in one way.

The holders for heart valves are relatively simple objects, generally manufactured of plastics. The holder is manufactured in one or two parts and, concerning the mechanical valve, the holder fits exactly in the opening of the valve, while the holders for biological valves are sutured onto the side of the valve.

Conventional holders for the double bladed heart valves face the problem that they can be mounted from both sides of the valve. When one handles an aortic valve, the holder must be placed on the opening side of the valve, while a mitral valve holder must be placed on the valve closing side. If the valve is positioned incorrectly in the heart, the passage is closed and the heart cannot pump. If the error is detected by the surgeon, the valve must be removed to the correct position, otherwise the patient cannot survive the operation.

To prevent an aortic valve holder being mounted from the wrong side, the safety member 20, according to the present invention, is provided so that it only fits from the opening side. To prevent a mitral valve holder from being mounted on the wrong side, a similar safety member 20 is provided for the mitral holder so that the holder can only be mounted from the closing side.

Although labels of different types are put on the packing or on the valve itself, they are not a guarantee that the correct valve size is used. According to the invention, the size of the valve ring is indicated by the holder, which besides having a visible number infused in the plastic at the production, also has the same color marking as the prosthesis sizer.

Figure 5:
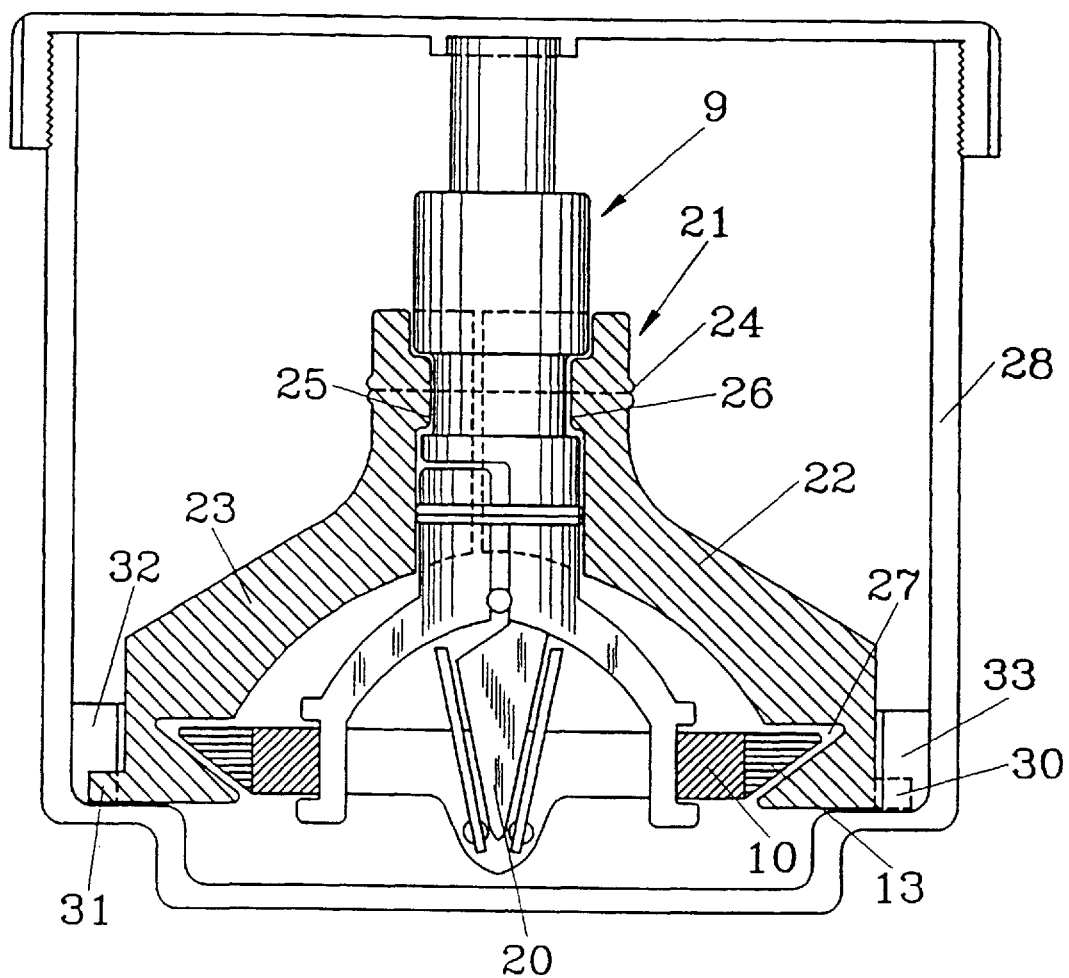
FIG. 5 shows a cross-sectional view of a holder with heart valve according to a modified embodiment, which is provided with a safety ring and placed in a transportation container.

To further ensure that a wrong size indication on the valve is not marked on the holder, a safety ring 21 is placed over the valve cuff 13 of the heart valve, as shown in FIG. 5. The safety ring 21 is made of two halves 22, 23 which are held together by a suture 24 and are removed before the valve is sutured firmly to the heart, while the holder 9 itself is removed after the valve has been placed in its final position in the heart.

The safety ring 21 is designed to fit only on one size of the holder. For example, by means of varying length L of a peripheral recess 25 and a corresponding projecting part 26 in the safety ring 21, where the length "L" is different for different valve sizes, such confusion can be avoided. If the holder is made in this way, a larger safety ring 21 cannot fit in the recess 25. Mounting a smaller ring in the holder is not possible, since the outer dimension of the valve is larger than the safety ring, which consequently will not fit across the valve cuff 13. Furthermore, on the holder as well as on the safety ring, a dimension number is infused in plastic and they are of same color.

As shown in FIG. 5, the safety ring 21 has an internal recess 27, the form of which fits the valve cuff 13. Since cuffs in mitral and aortic valves are different, usually with a larger cuff in the mitral valves and with different inclination profiles on the side, the safety ring will be a guarantee that the right type of valve is mounted on the holder. Thus, with this system, a mitral valve cannot be mounted in an aortic holder by mistake and an aortic valve cannot be mounted in a mitral holder, which is the case with present existent systems.

The holder of FIG. 5 guarantees that only valves of the correct size can be mounted on the holder, unlike prior art holders. This is particularly important because valve size is typically written on the packaging, but not on the valve itself.

The invention is very simple and relatively inexpensive. The new holders will not negatively effect the valves.

Generally, artificial heart valves are supplied in a transportation container 28 with the holder mounted to the valve. The holder has a double function, during the transportation it stabilizes the valve, and aids in the suturing of the valve to the heart.

As shown in FIG. 4 the shaft 29 of the holder is equipped with one or more outer fitting elements, which in this embodiment consists of peripheral recesses 30 and bars 31, which have a different width for every desired type and size holder. The transportation container 28 is provided with corresponding recesses 32 and bars 33. By varying the size and the number of the recesses and the distance between these, endless combinations are obtained, which allow only one special type of valve holder to fit the container. Thus, the valve holder cannot simply fit in the container without being of correct type, and confusion is prevented during packaging of the valve.

The recesses 30 and the ledges 31 can also be used for identification of the holder during production, if the tool handling the product is provided with corresponding details.

Also, the safety ring 21 can be provided with a fitting element, which is provided so that only the correct type of valve can fit into the container 28, which is exemplified in FIG. 5.

By providing the valve holder with these simple fitting elements the risk of a valve being placed in a wrong container is eliminated, assuming that the valve holder from the beginning is constructed so that only a correct valve can be mounted on the holder.

Due to different causes, a holder or a part thereof may rarely be left in the area of the operation and cause serious problems. To discover that some strange object of mentioned type is left in the body after the operation, preferably, the holder is made of a material which becomes visible by x-ray on a x-ray plate or screen. Another possibility is to add micro particles, having enough density that it can be detected by means of x-ray, to the plastic material during the manufacture of the holder. A third possibility is that to the exterior of the holder apply (infuse) small plates or the like, which become visible by means of x-ray. It is also possible to "mark" the holder using radiation, so that it can be detected if it should be left in the body.

When implanting the heart valve it can also be desired to change the part of the aorta that is directly connected to the valve. FIG. 6 shows a holder specially constructed for this purpose, which is provided with an extended handle portion 19 that is longer than the aortic prosthesis 34.

In certain cases biological heart valves are used, which require special holders, as shown in FIG. 7, which comprises a base plate 35 with peripheral flanges 36 to which the biological valve 37 is rigidly sewn with sutures. In a similar way as in other embodiments, base plate 35 provides safety member 20, which is provided to extend into the valve. At the handle portion 19, for instance, there is provided fitting elements 30 and 31, for cooperation with corresponding fitting elements of the transportation container.

I claim:

1. A holder for an artificial heart valve of the type having an inlet, an outlet and a first valve blade providing a first profile in relation to the inlet and a second profile in relation to the outlet, wherein the first profile and the second profile are different, the holder comprising:

a holder body configured to selectively couple to a heart valve;

a handle extending from the holder body; and a safety member, spaced apart from the holder body, extending from the handle and configured to mate with exactly one of the profiles when the holder body is in abutted contact with the heart valve, wherein the safety member prevents the holder body from mating with the other profile.

2. A holder according to claim 1 further comprising a first part and a second part, assembled with each other through a joint, and wherein the first part includes the handle.

3. A holder according to claim 2 wherein the second part is firmly fixed to the handle by a suture.

4. A holder according to claim 1 wherein the holder has a size and a shape, and the holder is marked by a color corresponding to the size and shape.

5. A holder according to claim 1 including a safety ring detachably mounted to the holder body and configured to surround an exterior of the heart valve, the safety ring having a shape corresponding to a shape of a periphery of the heart valve.

6. A holder according to claim 5 wherein the holder includes a recess and the safety ring includes a projecting part configured to fit into the recess.

7. A holder according to claim 5 wherein the safety ring includes a first fitting element configured to fit a transportation container for transporting a valve of a certain defined valve type and size.

8. A holder according to claim 7 wherein the first fitting element includes a bar configured to fit into a first recess of the transportation container.

9. A holder according to claim 1 wherein the holder body includes a material which is detectable through X-ray or through emission of detectable radiation.

10. A holder according to claim 1 wherein the safety member is configured to fit between the blade of the heart valve and a valve ring of the heart valve.

11. The holder according to claim 1 wherein the heart valve has a first state in which fluid flows through the heart valve, and a second state in which fluid is blocked from flowing through the heart valve, and wherein the safety member mates with the first profile when the valve is in the first state.

12. The holder according to claim 1 wherein the heart valve has a first state in which fluid flows through the heart valve, and a second state in which fluid is blocked from flowing through the heart valve, and wherein the safety member mates with the second profile when the valve is in the second state.

13. The holder according to claim 1 wherein the heart valve includes a second blade and wherein the safety member is configured to fit between the first and second blades.

* * * * *